United States Patent [19]
Faries, Jr. et al.

[11] Patent Number: 5,816,252
[45] Date of Patent: Oct. 6, 1998

[54] SURGICAL DRAPE LEAK DETECTION METHOD AND APPARATUS

[75] Inventors: Durward I. Faries, Jr., McLean, Va.; Bruce R. Heymann, Silver Spring, Md.

[73] Assignee: O.R. Solutions, Inc., Chantilly, Va.

[21] Appl. No.: 848,611

[22] Filed: Apr. 29, 1997

[51] Int. Cl.⁶ ................................................. A61B 19/00
[52] U.S. Cl. .............................................. 128/849; 4/655
[58] Field of Search ........................... 128/846, 849–856, 128/841, 844; 4/48.4, 452, 580, 655, DIG. 18; 62/66

[56] References Cited

U.S. PATENT DOCUMENTS

| | | |
|---|---|---|
| 3,902,484 | 9/1975 | Winters . |
| 4,393,659 | 7/1983 | Keyes et al. . |
| 4,474,016 | 10/1984 | Winchell . |
| 4,522,041 | 6/1985 | Menzel . |
| 4,782,835 | 11/1988 | Bernardini . |
| 4,934,152 | 6/1990 | Templeton . |
| 5,040,699 | 8/1991 | Gangemi . |
| 5,042,455 | 8/1991 | Yue et al. . |
| 5,163,299 | 11/1992 | Faries, Jr. et al. . |
| 5,174,306 | 12/1992 | Marshall . |
| 5,310,524 | 5/1994 | Campbell et al. . |
| 5,331,820 | 7/1994 | Faries, Jr. et al. . |
| 5,333,326 | 8/1994 | Faries, Jr. et al. . |
| 5,363,746 | 11/1994 | Gordon . |
| 5,374,813 | 12/1994 | Shipp . |
| 5,383,476 | 1/1995 | Peimer et al. . |
| 5,386,835 | 2/1995 | Elphick et al. . |
| 5,400,267 | 3/1995 | Denen et al. . |
| 5,400,616 | 3/1995 | Faries, Jr. et al. . |
| 5,402,644 | 4/1995 | Faries, Jr. et al. . |
| 5,429,801 | 7/1995 | Faries, Jr. et al. . |
| 5,435,322 | 7/1995 | Marshall . |
| 5,443,082 | 8/1995 | Mewburn . |
| 5,449,892 | 9/1995 | Yamada . |
| 5,457,962 | 10/1995 | Faries, Jr. et al. . |
| 5,463,213 | 10/1995 | Honda . |
| 5,502,980 | 4/1996 | Faries, Jr. et al. . |
| 5,522,095 | 6/1996 | Faries, Jr. et al. . |
| 5,524,478 | 6/1996 | Joy ............................................. 73/40 |
| 5,524,643 | 6/1996 | Faries, Jr. et al. . |
| 5,551,240 | 9/1996 | Faries, Jr. et al. . |
| 5,615,423 | 4/1997 | Faries, Jr. et al. . |
| 5,653,938 | 8/1997 | Faries, Jr. et al. . |

*Primary Examiner*—Michael A. Brown

[57] ABSTRACT

A sterile surgical drape for use with a system for thermally treating a sterile medium is accomplished by a drape including liquid sensitive material that changes color upon contact with liquid to indicate the presence of a leak. The liquid sensitive material may be placed between the drape and a receiving basin or affixed to the drape in the form of indicia symbolically directing placement of the drape over the system. The system may include a single basin and be of the type that either thermally cools or heats the sterile medium, or the system may include a plurality of basins with each basin either thermally cooling or heating the sterile medium. The drape typically includes liquid sensitive material affixed thereto in the form of various indicia indicating which portions of the drape are placed over the corresponding portions of the thermal treatment system. The indicia may further include symbols indicating the center of a basin, the direction to unfold the drape after removing the drape from its package, the proper orientation of the drape when placed on the system, and alignment of the drape on the system such that the drape overhangs the top surface of the system for a sufficient length to reduce the risk of contamination to the sterile medium. The liquid sensitive material detects leaks within the drape while assisting the operator in properly aligning and placing the drape over the system.

18 Claims, 4 Drawing Sheets

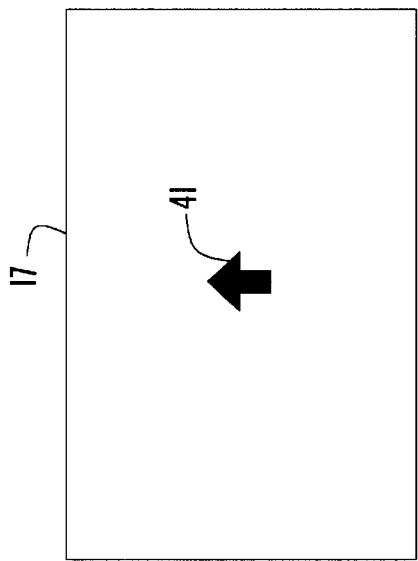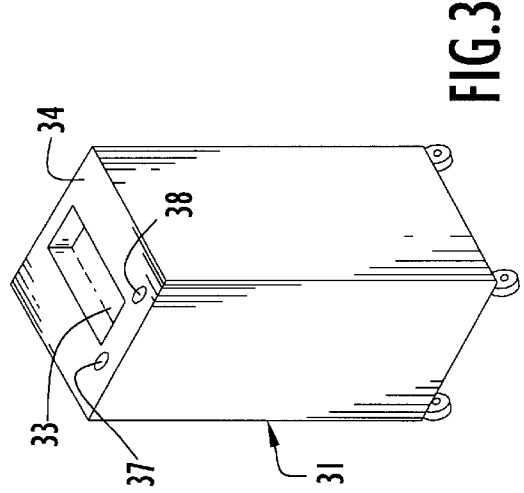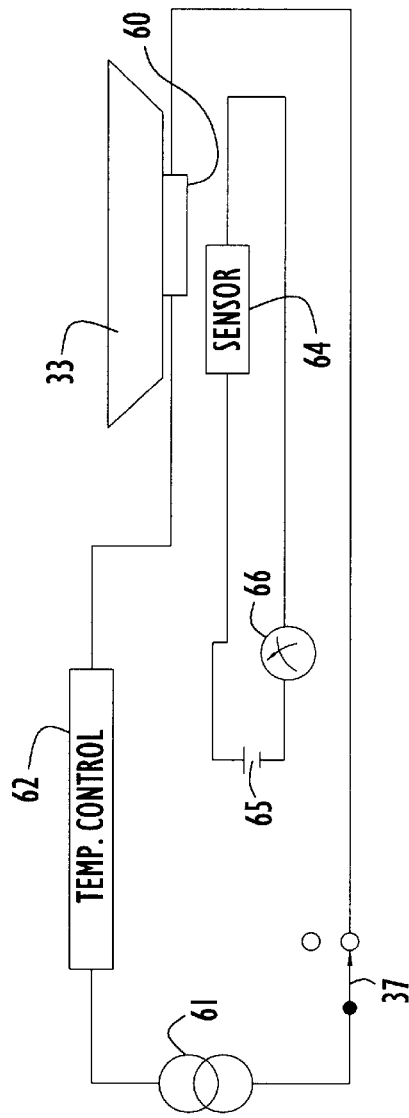

SURGICAL DRAPE LEAK DETECTION METHOD AND APPARATUS

BACKGROUND OF THE INVENTION

1. Technical Field

The present invention pertains to improvements in methods and apparatus for heating or cooling sterile surgical liquids and collecting surgical sterile slush. In particular, the present invention is an improvement of the methods and apparatus disclosed in U.S. Pat. Nos. 4,393,659 (Keyes et al), 4,934,152 (Templeton), 5,163,299 (Faries, Jr. et al), 5,331,820 (Faries, Jr. et al), 5,333,326 (Faries, Jr. et al), 5,457,962 (Faries, Jr. et al), 5,522,095 (Faries, Jr. et al), 5,524,643 (Faries, Jr. et al) and copending U.S. patent application Ser. No. 08/597,763 filed Feb. 7, 1996 entitled "Surgical Drape with Placement Indicia". The disclosures in those patents and copending patent application are expressly incorporated herein by reference in their entireties.

2. Discussion of the Prior Art

The above-referenced Keyes et al patent (U.S. Pat. No. 4,393,659) discloses a surgical slush producing system having a cabinet with a heat transfer basin at its top surface. A refrigeration mechanism in the cabinet takes the form of a closed refrigeration loop including: an evaporator in heat exchange relation to the outside surface of the heat transfer basin, a compressor; a condenser; and a refrigeration expansion control, all located within the cabinet. A separate product basin is configured to be removably received in the heat transfer basin. Spacers, in the form of short cylindrical stubs or buttons, are arranged in three groups spaced about the heat transfer basin and projecting into the heat transfer basin interior to maintain a prescribed space between the two basins. During use, that space contains a thermal transfer liquid, such as alcohol or glycol, serving as a thermal transfer medium between the two basins. A sterile drape, impervious to the thermal transfer medium, is disposed between the product basin exterior and the liquid thermal transfer medium to preserve the sterile nature of the product basin. Surgically sterile liquid, such as sodium chloride solution, is placed in the product basin and congeals on the side of that basin when the refrigeration unit is activated. A scraping tool is utilized to remove congealed sterile material from the product basin side to thereby form a slush of desired consistency within the product basin. Some users of the system employ the scraping tool to chip the solid pieces from the basin side.

As noted in the above-referenced Templeton patent (U.S. Pat. No. 4,934,152), the Keyes et al system has a number of disadvantages. In particular, the separate product basin must be removed and re-sterilized after each use. Additionally, the glycol or other thermal transfer medium is highly flammable or toxic and, in any event, complicates the procedure. The Templeton patent (U.S. Pat. No. 4,934,152) discloses a solution to these problems by constructing an entirely new apparatus whereby the product basin is eliminated in favor of a sterile drape impervious to the sterile surgical liquid, the drape being made to conform to the basin and directly receive the sterile liquid. Congealed liquid is scraped or chipped from the sides of the conformed drape receptacle to form the desired surgical slush.

The Faries, Jr. et al patent (U.S. Pat. No. 5,163,299) notes that scraping congealed liquid from the drape is undesirable in view of the potential for damage to the drape, resulting in a compromise of sterile conditions. As a solution to the problem, the Faries, Jr. et al patent (U.S. Pat. No. 5,163,299) proposes that the drape be lifted or otherwise manipulated by hand to break up the congealed liquid adhering to the drape. Although this hand manipulation is somewhat effective, it is not optimal, and often is inconvenient and constitutes an additional chore for operating room personnel.

The Faries, Jr. et al patent (U.S. Pat. No. 5,33 1,820) resolves the problem of manual manipulation of the drape by providing several techniques to automatically remove the congealed liquid adhering to the drape without endangering the integrity of the drape. For example, one such technique includes providing a flat disk or plate at the bottom of the basin under the drape, wherein the plate is moved in an up and down manner to disengage the congealed liquid from the drape. The plate may be attached to a mechanism below the basin, or to the drape itself as disclosed in the Faries, Jr. et al patent (U.S. Pat. No. 5,457,962).

The Templeton patent (U.S. Pat. No. 4,934,152) further discloses an electrical heater disposed at the bottom of the basin to convert the sterile slush to warmed liquid, or to heat additional sterile liquid added to the basin. Templeton describes the need for such warm sterile liquid as occurring after a surgical procedure is completed to facilitate raising the body cavity of the surgery patient back to its normal temperature by contact with the warmed liquid. However, there are a number of instances during a surgical procedure when it is desirable to have simultaneous access to both warmed sterile liquid and sterile surgical slush. Accordingly, the Faries, Jr. et al patents (U.S. Pat. Nos. 5,333,326 and 5,522,095) disclose a manner in which to simultaneously provide both surgical slush and warmed surgical liquid during a surgical procedure by utilizing a machine having multiple basins with each basin either producing surgical slush or heating a sterile liquid. This machine typically utilizes a single surgical drape that forms a drape receptacle within each basin to collect sterile slush and heated sterile liquid produced by the machine in the respective basins.

The above-described apparatus may stand some improvement since there is no provision for a simple and inexpensive way to detect leaks in a surgical drape while assisting in proper placement and orientation of the drape onto a thermal treatment machine. Since only sterile drapes are to be used during surgical procedures, a leak in a surgical drape compromises sterility and contaminates the entire surgical procedure, thereby increasing risk of injury to the patient. Although the Faries, Jr. et al patent (U.S. Pat. No. 5,524,643) discloses a system that detects leaks in drapes, that system employs sensors interfacing a microprocessor wherein the microprocessor performs a series of processes to interpret the sensor readings and determine whether or not a leak is present. Thus, the leak detection system of the Faries, Jr. et al patent (U.S. Pat. No. 5,524,643) is relatively sophisticated requiring several hardware components and processing to determine the presence of leaks within a drape. In addition, the Faries, Jr. et al patent (U.S. Pat. No. 5,522,095) and copending U.S. patent application Ser. No. 08/597,763 disclose drapes bearing indicia for directing proper placement of a drape onto a thermal treatment machine, however, the indicia only indicate proper placement of the drape onto the thermal treatment machine without performing other useful functions.

OBJECTS AND SUMMARY OF THE INVENTION

Accordingly, it is an object of the present invention to detect the presence of leaks within a surgical drape utilized to collect a sterile medium in a thermal treatment machine basin by affixing a liquid sensitive material to the surgical drape that changes color upon contact with liquid to indicate the presence of a leak within the surgical drape.

It is another object of the present invention to detect the presence of leaks within a surgical drape and direct proper placement of the surgical drape onto a thermal treatment machine by affixing a liquid sensitive material to the surgical drape wherein the liquid sensitive material is in the form of various indicia to indicate proper placement and/or orientation of the drape on the thermal treatment machine.

The aforesaid objects are achieved individually and in combination, and it is not intended that the present invention be construed as requiring two or more of the objects to be combined unless expressly required by the claims attached hereto.

According to the present invention, a drape including liquid sensitive material is disposed over a top surface of a thermal treatment system having a basin recessed in a top surface of the system. A portion of the drape is pushed down into, and conforms to, the basin to form a drape container or receptacle within the basin for collecting a sterile medium. The thermal treatment system may be of the type that either congeals or heats the sterile medium to respectively produce sterile slush or a warm sterile liquid within the basin. The liquid sensitive material is typically disposed on the non-sterile side of the drape and positioned within the basin between the drape container and the basin, wherein the liquid sensitive material changes color upon contact with liquid to indicate the presence of liquid external of the drape container (i.e., between the drape and the basin) or, in other words, the existence of a leak. The material may be adhered to one or more locations of the drape as dots or strips or other configurations, or it may simply be placed in the basin prior to installation of the drape. Further, the liquid sensitive material, if adhered to the underside of the drape, may be in the form of various shapes and indicia to indicate proper placement and/or orientation of the drape on the system. In addition, the liquid sensitive material may be affixed to a drape utilized for a multiple basin thermal treatment system wherein each basin may either congeal or heat the sterile medium as described above. The multiple basin drape forms a drape receptacle within each basin wherein liquid sensitive material is typically disposed between each drape receptacle and basin to detect the presence of a leak within each basin in substantially the same manner described above for the single basin system.

The above and still further objects, features and advantages of the present invention will be apparent upon consideration of the following detailed description of the specific embodiments thereof, particularly when taken in conjunction with the accompanying drawings wherein like components are designated by like reference numerals.

BRIEF DESCRIPTION OF THE DRAWINGS

FIG. 3 is a view in perspective of a thermal treatment system of the type employed by the present invention for warming a sterile medium.

FIG. 4 is an electrical schematic diagram of a heating unit employed in the thermal treatment system of FIG. 3.

FIGS. 5–14 are views in plan of exemplary surgical drapes bearing liquid sensitive material for detecting leaks within the drapes and designating the orientation of the drapes and/or center of a thermal treatment system basin for proper placement of the drapes over the thermal treatment system.

DETAILED DESCRIPTION OF THE PREFERRED EMBODIMENTS

Figure 1:
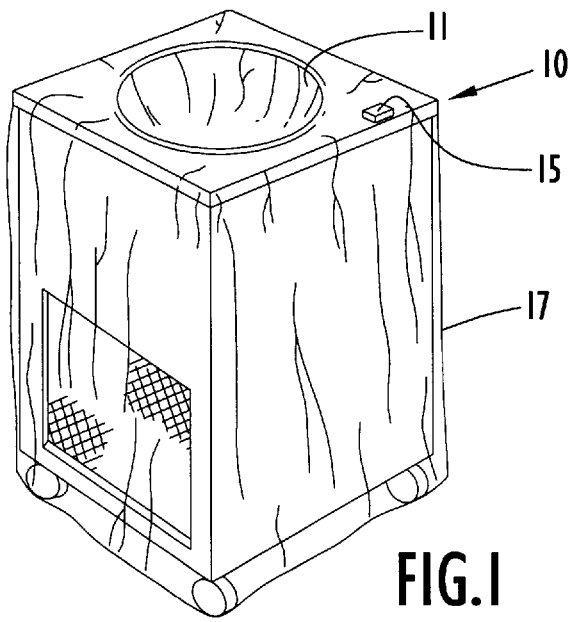
FIG. 1 is a view in perspective of a thermal treatment system and corresponding surgical drape of the type employed by the present invention for generating and collecting surgical slush.
Figure 2:
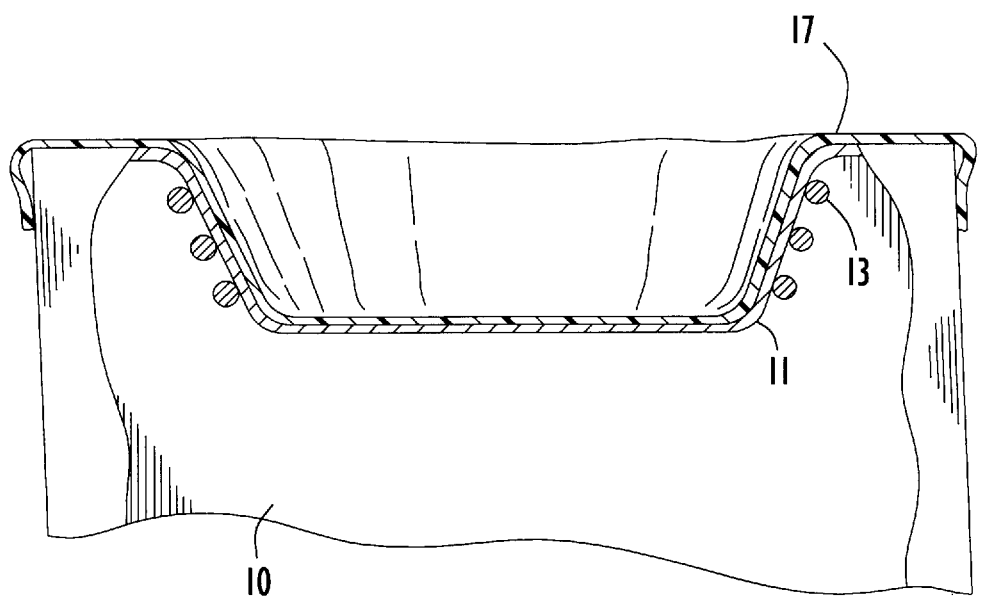
FIG. 2 is a view in elevation and partial section of the thermal treatment system and surgical drape of FIG. 1.
Figure 6:
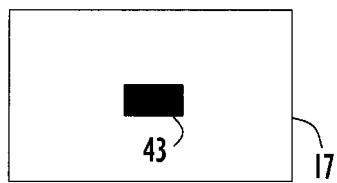
Figure 7:
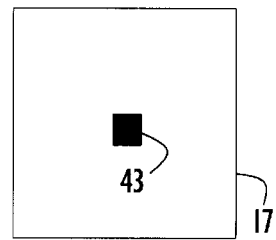
Figure 8:
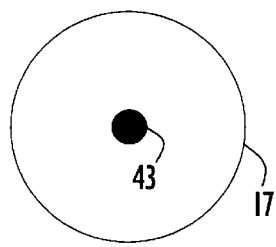
Figure 9:
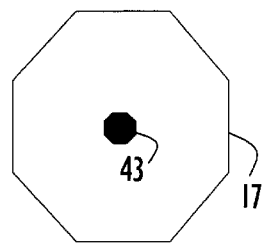

Referring to FIGS. 1–2 of the accompanying drawings, a thermal treatment machine or system for generating surgical slush of the type described in the above-referenced Templeton patent includes a cabinet or housing 10 with a top surface having a basin 11 mounted thereon in an appropriately sized recess. Basin 11 is made of thermally conductive material, typically stainless steel, and includes a generally flat bottom wall and frusto-conical side wall. A conventional refrigeration unit is disposed within cabinet 10 and typically includes a compressor, a condenser and an expansion control unit connected by appropriate fluid conduits in a closed refrigeration loop of evaporator 13. The evaporator is in the form of a coil wound about the exterior surface of basin 11 in thermal transfer relation therewith. The refrigeration unit is activated by means of appropriate controls 15, while evaporator 13 cools the side wall of basin 11 to a temperature substantially below the freezing temperature of the liquid used in forming the sterile slush. This temperature is preferably on the order of −32° F. to 10° F. For further details of the structure and operation of the refrigeration unit, reference is made to the aforementioned Keyes et al and Templeton et al patents.

A typical thermal treatment system for heating a sterile medium (i.e., liquid) employed by the present invention is illustrated in FIG. 3. Specifically, the system includes a cabinet or housing 31 and a warming basin 33 recessed into a top surface 34 of cabinet 31. Basin 33 may be of any shape, however, by way of example only, the basin is illustrated as being substantially rectangular. A heater power switch 37 and a temperature controller/indicator 38 are provided on top surface 34 adjacent the warming basin. It is to be understood that the thermal treatment systems described above may have various configurations (e.g., varying basin shapes) and include a plurality of basins warming and/or cooling a sterile medium as described above. An example of such a system is disclosed in the aforementioned Faries, Jr. et al patents (U.S. Pat. No. 5,333,326 and 5,522,095).

The manner of heating sterile liquid in warming basin 33 is illustrated schematically in FIG. 4. Specifically, an electrical circuit includes a power source 61 connected in series with a temperature control unit 62, a heater element or pad 60, and power control switch 37. Heater 60 is typically a thin wafer-like member disposed along the bottom surface of heating basin 33, secured to the basin by a suitable pressure sensitive adhesive having efficient heat transfer characteristics. Heater 60 has smaller dimensions than the basin bottom and is disposed at the approximate center of the bottom surface of the basin. The heater, for example, may be of the type described in the aforementioned Templeton patent. Temperature control unit 62 includes a device for adjusting current passing through the heating element 60 so as to permit selective adjustment of the heat applied to the liquid in basin 33. The power switch 37 permits selective application and removal of current flow with respect to heater 60.

A temperature sensor 64 is disposed adjacent basin 33 to sense the temperature of the liquid therein. Sensor 64 is connected in series with a voltage source 65 and an indicator 66. Voltage source 65 and power source 61 may be the same source, or the voltage for one may be derived from the other. Indicator 66 measures the current through temperature sensor 64, that current being proportional to the sensed temperature. Indicator 66 and temperature controller 62 may correspond, for example, to the temperature controller/indicator 38 described above. For further details on the operation of the heating unit, reference is made to the Faries, Jr. et al (U.S. Pat. No. 5,333,326) and other above-mentioned patents.

Referring back to FIG. 1, a sterile drape 17, preferably transparent, is typically disposed over the top and sides of cabinet 10 and made to conform to the side wall and bottom of basin 11. Controls 15 are disposed on the top surface of system cabinet 10 and are adjustable manually through drape 17. The portion of drape 17 disposed in basin 11 serves as a sterile receptacle for sterile liquid placed therein to be frozen into the desired sterile slush. Drape 17 is also utilized by, and disposed over the top surface of, the thermal treatment system of FIG. 3 in substantially the same manner described above wherein a portion of drape 17 is disposed within basin 33 to form a receptacle for collecting heated sterile liquid. Typical sterile liquid used to produce a surgical sterile slush or a heated sterile liquid is a 0.80% to 0.95% sodium chloride solution (i.e., saline). Drape 17 is made from a material that is impervious to the sterile liquid and sufficiently soft and flexible to conform to a basin wall. The thickness of the drape is preferably minimized to render thermal transfer therethrough most efficient, yet the thickness is sufficient to resist tearing and puncturing during, normal use. Typically, by way of example only, the drape may be made of materials commonly used in hospitals for surgical drapes and has a thickness in the range of three through ten mils. Drape 17 may also be made of polyurethane film as disclosed for the drape in the aforementioned Templeton patent. The drape may further include a preformed container portion contoured to match the contour of a basin. The preformed container portion is typically thicker than the remaining portions of the drape described above in order to resist puncture and enable the container portion to maintain the shape of the basin. By way of example only, the container portion may be made of a heavy gauge polyethylene/ionomer resin blend having a thickness of approximately ten through sixteen mils. The percentage of ionomer resin in the blend is approximately in the range between forty and seventy percent. The drape is designed to be disposable after a single use and is provided presterilized and prepackaged in a manner to preserve its sterile state during storage.

The drape is typically positioned over a thermal treatment system with a portion of the drape disposed in a basin to form a drape receptacle as described above. The drape forms a sterile field above the basin to maintain sterility of the sterile medium. However, a puncture, tear or other opening in the drape disrupts the sterile field and may contaminate the sterile liquid, thereby risking injury to a patient. In order to detect leaks within the drape and maintain sterility of the sterile medium, drape 17 includes a liquid sensitive material that changes color upon contact with liquid. The material is typically disposed on the non-sterile drape surface (i.e., the surface opposite the sterile medium and facing the basin walls) to detect the presence of liquid beneath the drape, thereby indicating the existence of a leak. The portion of drape 17 containing the liquid sensitive material is disposed in a thermal treatment system basin to form a drape receptacle as described above such that the liquid sensitive material is disposed between the drape receptacle and basin. Since drape 17 is preferably transparent or translucent, the color change of the material, upon contact with liquid, is readily visible by an operator, thereby providing a clear and noticeable indication that the drape contains a leak. In addition, the color change of the material is imputed to the otherwise clear liquid, thereby altering the liquid color and providing a further indication of the existence of a leak. Alternatively, the liquid sensitive material may be independently disposed in the basin with the drape receptacle then placed over the liquid sensitive material within the basin for detecting leaks in substantially the same manner described above. The liquid sensitive material typically includes small section affixed to the drape in multiple locations, or a large section affixed to the drape in a particular location, however, the liquid sensitive material may be partitioned and disposed on the drape in any manner capable of detecting leaks within a drape.

The liquid sensitive material implements well known techniques of test strips or other types of detectors utilizing color change as a detection mechanism for indicating the presence of different substances within liquids or of liquids. For example, U.S. Pat. No. 3,963,442 (Bullard et al) discloses test strips having a first reagent that reacts with a second reagent within a liquid to produce a color change. In effect, this test strip detects the presence of the second reagent within a liquid and changes color to indicate the presence of that second reagent. Further, U.S. Pat. No. 5,491,094 (Ramana et al) discloses a test strip that changes color to indicate the free available chlorine concentration within a liquid. The foregoing Bullard and Ramana patents are incorporated herein by reference in their entireties. The liquid sensitive material of the present invention utilizes similar techniques, but is preferably implemented by test strips manufactured and sold as "Waterworks 5" by Industrial Test Systems, Inc. of Rock Hill, S.C.

The liquid sensitive material may further be affixed to drape 17 in various manners to indicate the center of a thermal treatment system basin and/or orientation of the drape for proper placement of the drape onto the thermal treatment system. An exemplary drape 17, suitable for covering the top surface of a thermal treatment system and including liquid sensitive material for detecting leaks as described above and symbolically directing an operator in unfolding the drape when removed from its package is illustrated in FIG. 5. Specifically, drape 17 is substantially similar to the drape described above except that drape 17 further includes liquid sensitive material 41 disposed on the drape for detecting the presence of leaks within the drape and assisting an operator to properly unfold drape 17 into the proper orientation for placement over a thermal treatment system. Initially, drape 17 is folded in order to be efficiently and securely stored in packaging for preservation of its sterile state during shipment, distribution and storage. When a nurse or other operating room personnel opens the drape package, liquid sensitive material 41 disposed on a folded non-sterile side of drape 17 and visible to the nurse, indicates the position or direction to unfold drape 17 for proper orientation and placement of the drape over the thermal treatment system cabinet. Liquid sensitive material 41 may be any shape or symbol indicating the position or direction for unfolding, and is generally strategically disposed on a portion of drape 17 representing the approximate center of a drape receptacle to ensure detection of liquid in response to the existence of a leak in the drape. By way of example, liquid sensitive material 41 is disposed at the approximate center of drape 17 for use with a thermal treatment system having basins substantially centered on its top surface, however, the liquid sensitive material may be disposed on the drape in any manner to accommodate a thermal treatment system having a basin disposed at other locations on its top surface. Typically, liquid sensitive material 41 is formed into a symbol substantially similar to an arrow pointing toward the intended unfolding direction.

Figure 11:
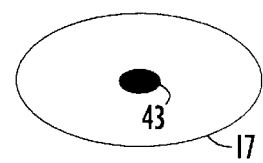

The liquid sensitive material may also be disposed on a sterile drape in order to assist the operator in properly orientating the drape relative to a thermal treatment system basin as illustrated in FIGS. 6–11. Specifically, an exemplary drape 17 is substantially similar to the drape having liquid sensitive material indicating the manner in which to unfold the drape as described above except that drape 17 includes liquid sensitive material in the form of indicia for properly orienting the drape onto a thermal treatment system and detecting leaks within the drape as described above. Orientation indicia 43 are typically disposed on a portion of drape 17 representing the approximate center of a drape receptacle, and preferably have the shape of the particular basin utilized in the corresponding thermal treatment system. By way of example, indicia 43 are disposed at the approximate center of drape 17 for use with a thermal treatment system having a basin substantially centered on its top surface, however, the orientation indicia may be disposed on the drape in any manner to accommodate a thermal treatment system having a basin disposed at other locations on its top surface. The basin of the thermal treatment system may be of any shape and therefore the configurations of orientation indicia 43 preferably vary in accordance with the shape of the particular basin. For example, the basin and indicia may be rectangular (FIG. 6), square (FIG. 7), circular (FIG. 8), octagonal (FIG. 9), hexagonal (FIG. 10) or oval (FIG. 11). Although the periphery of each drape is a larger version of the shape of indicia 43 and hence the basin to be covered, such is not necessarily the case (i.e., circular symbol 43 can be used with a square drape, etc.). The size of indicia 43 may be the same as the basin size but is preferably much smaller and positioned to be centered in the basin in order to ensure detection of liquid beneath the drape container when the drape is pushed down into and conforms to the basin to form a drape receptacle. Drape 17 is generally manipulated such that orientation indicia 43 correspond to the orientation of a corresponding thermal treatment system basin for proper placement of the drape over the thermal treatment system. A potion of drape 17 containing indicia 43 is disposed within the basin to form a drape receptacle such that indicia 43 is positioned at the approximate basin center to detect the presence of leaks within the drape as described above.

Figure 12:
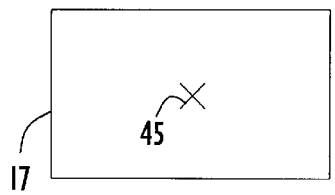
Figure 13:
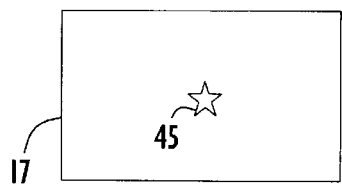

In order to reduce the risk of contamination that would result if a sterile drape incurs leaks or is not positioned properly on a top surface of a thermal treatment system cabinet, the drape may include liquid sensitive material in the form of indicia for proper center and alignment of the drape on the top surface of a thermal treatment system as illustrated in FIGS. 12–13. Specifically, an exemplary drape 17 is substantially similar to the drapes as described above except that drape 17 includes leak detecting liquid sensitive material 45 in the form of indicia for properly aligning the drape with respect to the center of the basin such that the drape uniformly overhangs the top surface by a length sufficient to maintain sterility of the sterile field and does not inadvertently move relative to the cabinet. These alignment indicia are typically disposed on the non-solution receiving side of drape 17 to detect the presence of a leak within the drape as described above and for greater visibility to the nurse. The alignment indicia may include any variations of symbols that are capable of directing an operator toward the proper alignment of the drape.

For example, drape 17 may include liquid sensitive material in the form of alignment indicia disposed at the approximate center of the drape, usually to facilitate placing of that indicia at the approximate center of the basin to detect liquid beneath the drape container and indicate the presence of a leak. Specifically, special symbols 45, typically an "X" (FIG. 12) or star (FIG. 13), may be placed at the approximate center of drape 17 on the non-sterile side. Surrounding portions of drape 17 adjacent special symbols 45 are pushed down into the basin subsequent to placement of drape 17 on the top surface of the cabinet. Once the drape portion bearing special symbols 45 is pushed down into and positioned at the approximate center of the lowermost portion or bottom of the basin, drape 17 overhangs the top surface of the cabinet uniformly in all directions by a sufficient length to maintain sterility of the sterile field. In certain instances, depending upon the particular thermal treatment system being employed, a bolt or plug may reside at the approximate center of the lowermost portion or bottom of the basin. In these instances, special symbols 45 may be positioned coincident the bolt or plug for proper placement of drape 17 over the cabinet. In the absence of any such center indications in the basin, the operator must estimate the location of the approximate center of the basin for aligning the special symbols 45. By way of example, symbols 45 are disposed at the approximate center of drape 17 for use with a thermal treatment system having a basin substantially centered on its top surface, however, the special symbols may be disposed on the drape in any manner to accommodate a thermal treatment system having a basin disposed at other locations on its top surface.

Figure 14:
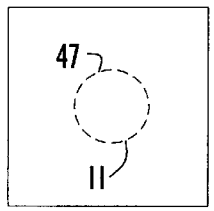
Figure 10:
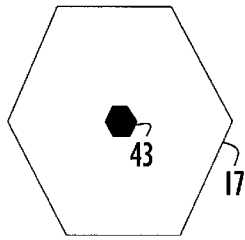
Figure 15:
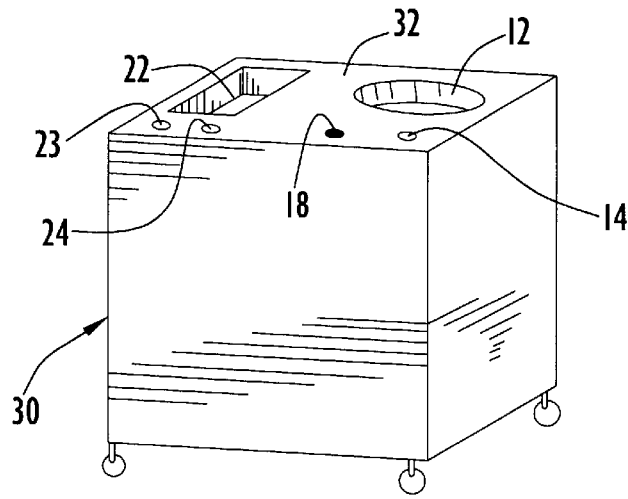
FIG. 15 is a view in perspective of a multiple basin thermal treatment system of the type employed by the present invention for heating and/or cooling a sterile medium.
Figure 16:
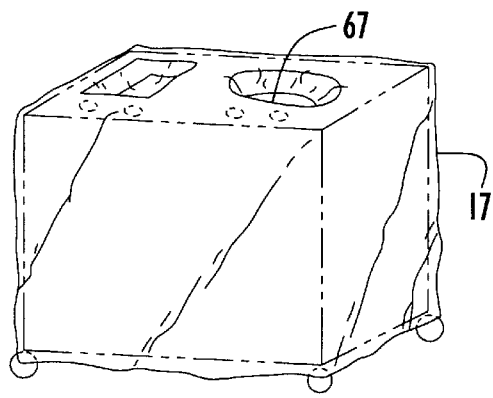
FIG. 16 is a view in perspective of a surgical drape positioned over the thermal treatment system of FIG. 15 according to the present invention.

Alternatively, the alignment indicia may include an outline of the lowermost portion of the basin as illustrated in FIG. 14. Liquid sensitive material 47 is disposed on an exemplary drape 17 in the form of a dotted or whole line circle that specifically represents the actual lowermost basin periphery. Drape 17 is aligned by determining the orientation of the drape and subsequently placing the drape over the top surface of the thermal treatment system. The portion of drape 17 within the outline of the basin is pushed down into the basin until the outline of the lowermost portion of the basin is coincident the lowermost portion of the basin. Alignment indicia 47 may be disposed on the drape in any manner to accommodate thermal treatment systems having basins disposed in their top surfaces at various locations A surgical drape 17 with liquid sensitive material in the form of indicia suitable for use with a thermal treatment system having a plurality of basins is illustrated in FIGS. 15–16. Initially, an exemplary thermal treatment system having multiple basins for simultaneously cooling and heating sterile liquid has an integral assembly 30 including a slush basin 12 for slush phase medium and a warming basin 22 for heated liquid phase medium recessed into top surface 32 of a common cabinet. Also disposed in top surface 32 are a cooling unit power switch 18, a cooling unit temperature controller/indicator 14, a heater power switch 23 and a heater unit temperature controller/indicator 24. For further details of the structure and operation of assembly 30, reference is made to the aforementioned Faries, Jr. et al patents (U.S. Pat. No. 5,333,326 and 5,522,095).

Figure 17:
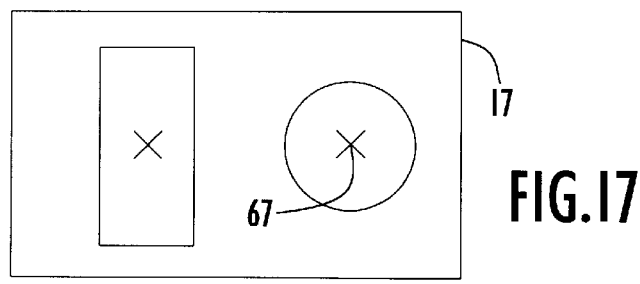
FIG. 17 is a view in plan of a exemplary surgical drape bearing liquid sensitive material for detecting leaks within the drape and designating the orientation of the drape and/or center of each thermal treatment system basin for proper placement of the drape over the thermal treatment system of FIG. 15.

A drape 17 for use with the plural basin system is substantially similar to the drapes described above but is of sufficient size to encompass the plurality of basins as illustrated in FIGS. 16–17. Specifically, drape 17 may include liquid sensitive material in the form of alignment indicia substantially similar to any of the aforementioned alignment indicia described above. The alignment indicia are preferably present for all basins of the plural basin system to detect leaks in the drape within each basin as described above and to ensure consistent alignment of the drape on the plural basin system. For example, the alignment indicia may include indicia 67 that are substantially similar to special symbol 45 of FIG. 12 described above. Indicia 67 indicate the approximate center of the basins and are not necessarily disposed at the approximate center of drape 17. This allows drape 17 to achieve optimal positioning in the basins while ensuring that the drape overhangs the top surface of the plural basin system by a sufficient length to maintain sterility and not interfere with vents on the sides of the plural basin system. Drape 17 is aligned by determining the proper orientation of the drape and placing the drape over the top surface of the plural basin system in order to push portions of the drape coincident the basins down into each of the basins until basin indicia 67 are properly positioned at the approximate center of the lowermost portion or bottom of the basins. Further, drape 17 may accommodate any number of heated and/or cooled basins in a thermal treatment system in substantially the same manner described above. Moreover, drape 17 for the plural basin system may include liquid sensitive material in the form of any of the above-mentioned orientation, fold, alignment or other indicia implemented in substantially the same manner described above to detect leaks within the drape and direct proper placement of the drape onto the plural basin system.

Several techniques may be employed to dispose the liquid sensitive material on the drape. For example, the liquid sensitive material may be affixed to the drape by use of conventional adhesives or any other known affixation techniques. Moreover, the drape may include liquid sensitive material in the form of one or more of the aforementioned indicia in any combination or permutation. In addition, the liquid sensitive material in the form of the aforementioned indicia may be disposed on a drape typically having a size greater than needed for the thermal treatment system. The operator aligns the drape on the thermal treatment system in a substantially similar manner for the respective indicia as described above and, if necessary, may cut the drape to an appropriate length for the specific thermal treatment system employed. The drape may therefore be compatible with numerous thermal treatment systems and ensures a consistent length and fit.

It will be appreciated that the embodiments described above and illustrated in the drawings represent only a few of the many ways of implementing a surgical drape with liquid sensitive material for detecting leaks within the drape.

The drape may include any material capable of collecting sterile medium (i.e., impervious to liquid) and maintaining sterility. Further, the drape may be constructed to be utilized for any number of basins and include the liquid sensitive material for each basin.

The liquid sensitive material may be any material, compound or other detector that changes color or provides another noticeable indication upon contact with liquid, and may be in the form of any indicia capable of being readily visible. Further, the liquid sensitive material may be separate from the drape and disposed in thermal treatment system basins, or may be removably or permanently affixed to the drape by processes including but not limited to glue or other adhesive material, formed as part of the drape, or any other known affixation method. Moreover, the indicia may be constructed from any liquid sensitive or other material that indicates the presence of a leak (i.e., detects the presence of liquid or solution). In addition, the liquid sensitive material may be in the form of any indicia and may include any symbols, characters, words etc. indicating the proper positioning of the drape on a thermal treatment system and is not limited to the specific symbols disclosed herein.

From the foregoing description it will be appreciated that the invention makes available a novel surgical drape wherein the drape includes liquid sensitive material in the form of indicia for indicating proper placement of the drape over a thermal treatment system and detecting leaks within the drape.

Having described preferred embodiments of a new and improved surgical drape leak detection method and apparatus, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A surgical drape for use in a thermal treatment system thermally treating a sterile liquid or slush medium and including a basin recessed in a top surface of a system housing for collecting said sterile medium, said drape comprising:

a drape portion for covering and hanging down from said top surface of said system housing, wherein said drape portion is pushed down into and conforms to said basin to form a drape receptacle; and leak detection material disposed between said drape and said basin for visually indicating the presence of a leak through said drape by changing color in response to contact with said sterile medium.

2. The drape of claim 1 wherein said leak detection material is affixed to said drape receptacle and includes liquid sensitive material that changes color upon contact with said sterile medium wherein said liquid sensitive material is in the form of indicia symbolically directing placement of said drape portion over said top surface.

3. The drape of claim 2 wherein said indicia include orientation indicia designating the proper orientation of the drape on said top surface.

4. The drape of claim 2 wherein said indicia include centering indicia indicating the center of said basin and the drape portion to be pushed down into said basin to form said drape receptacle such that said centering indicia reside at the center of said basin.

5. The drape of claim 2 wherein said indicia include fold indicia designating a direction said drape is to be unfolded for proper orientation on said system.

6. The drape of claim 1 wherein:

said system further includes a plurality of basins recessed in said top surface;

said drape portion is pushed down into and conforms to each said basin to form said drape receptacle within each said basin; and said drape includes a plurality of said leak detection means wherein each said leak detection means is affixed to a corresponding drape receptacle formed within one of said basins to indicate the presence of said leak in said drape.

7. In a thermal treatment system including a basin for containing a sterile liquid or slush medium and a sterile drape for placement over a top surface of said system to collect said sterile medium, a method of detecting leaks within said drape comprising the steps of:

(a) disposing leak detection material between said drape and said basin to detect leaks through said drape wherein said leak detection material changes color to indicate the presence of said leak;

(b) placing said drape over said top surface and pushing portions of said drape coincident said basin into said basin such that said drape conforms to said basin and forms a drape receptacle for containing said sterile medium, wherein said leak detection material is disposed between said drape receptacle and said basin; and (c) monitoring said leak detection material for a change in color to determine the presence of said leak through said drape.

8. The method of claim 7 wherein said leak detection material includes a liquid sensitive material, and step (a) further includes:

(a.1) affixing said liquid sensitive material to said drape wherein said liquid sensitive material changes color upon contact with said sterile medium and is in the form of indicia symbolically directing placement of said drape over said top surface.

9. The method of claim 8 wherein said indicia include unfolding indicia designating the direction to unfold said drape for proper orientation on said top surface, and step (b) further includes:

(b.1) removing said drape from said package and unfolding said drape in the direction indicated by said unfolding indicia for proper orientation of said drape on said top surface.

10. The method of claim 8 wherein said indicia include centering indicia indicating the center of said basin, and step (b) further includes:

(b.1) aligning said centering indicia over the center of said basin, and (b.2) pushing portions of said drape coincident said basin into said basin until said centering indicia is positioned at the bottom center of said basin.

11. The method of claim 8 wherein said indicia include orientation indicia in the shape of said basin, and step (b) further includes:

(b.1) manipulating said drape such that said orientation indicia correspond to the orientation of said basin; and (b.2) placing said manipulated drape over said top surface such that said orientation of said drape is aligned with said orientation of said basin.

12. The method of claim 7 wherein said system further includes a plurality of basins, and step (a) further includes:

(a.1) affixing a plurality of said leak detection material to said drape;

step (b) further includes:

(b.1) pushing portions of said drape coincident said plurality of basins into said plurality of basins such that said drape conforms to said basins and forms a drape receptacle within each said basin, wherein each said leak detection material is disposed in a corresponding basin between each said drape receptacle and each said basin to indicate the presence of said leak within said drape; and step (c) further includes:

(c.1) monitoring said plurality of leak detection material to determine the presence of said leak within said drape.

13. A method for detecting a leak within a drape positioned over a top surface of a thermal treatment system having a basin for containing a sterile liquid or slush medium, said method comprising the steps of:

(a) forming a surgical drape configured to overlie the top surface of the system with a portion of the drape recessed into the basin to define a drape receptacle in the basin for the sterile medium; and (b) disposing leak detection material in said basin, said leak detection material changing color upon contact with said sterile medium to indicate the presence of a leak in the drape.

14. The method of claim 13 wherein said leak detection means includes liquid sensitive material and step (b) further includes:

(b.1) affixing said liquid sensitive material to said drape in the form of indicia to designate a direction for properly unfolding said drape into a proper orientation for placement of said drape on the top surface of the system.

15. The method of claim 13 wherein said leak detection means includes liquid sensitive material and step (b) further includes:

(b.1) affixing said liquid sensitive material to said drape in the form of centering indicia indicating the center of the basin such that said drape is properly aligned on the top surface of the system when said centering indicia are positioned at the center of the bottom of the basin.

16. The method of claim 13 wherein said system further includes a plurality of basins, and step (b) further includes:

(b.1) affixing a plurality of said leak detection means to said drape wherein each said leak detection means is disposed in a corresponding basin to indicate the presence of said leak within that basin.

17. The method of claim 13 wherein said leak detection means includes liquid sensitive material and step (b) further includes:

(b.1) affixing said liquid sensitive material to said drape in the form of orientation indicia indicating the orientation of the drape relative to the basin to direct proper placement of the drape on the top surface of the system.

18. In a thermal treatment system including at least one basin for containing a sterile liquid or slush medium and a sterile drape for placement over a top surface of said system to collect said sterile medium, wherein said drape is pushed down into and conforms to each said basin to form a drape receptacle within each said basin for containing said sterile medium, a method of detecting a leak within said drape comprising the step of:

(a) affixing liquid sensitive material to each said drape receptacle wherein said liquid sensitive material changes color upon contact with said sterile medium, and monitoring said liquid sensitive material for a color change that indicates the presence of said leak.

* * * * *